United States Patent
Heesch et al.

(10) Patent No.: US 10,714,871 B2
(45) Date of Patent: Jul. 14, 2020

(54) ANESTHESIA APPARATUS OR VENTILATOR WITH A HOT WIRE SENSOR, HOT WIRE SENSOR AND HOT WIRE SENSOR MODULE FOR A HOT WIRE SENSOR

(71) Applicant: Drägerwerk AG & Co. KGaA, Lübeck (DE)

(72) Inventors: Ralf Heesch, Lübeck (DE); Bernd Kellner, Rohlstorf (DE); Henning Gerder, Lübeck (DE); Thomas Reßing, Ratekau (DE); Andreas Timmann, Lübeck (DE)

(73) Assignee: DRÄGERWERK AG & CO. KGAA, Lübeck (DE)

( * ) Notice: Subject to any disclaimer, the term of this patent is extended or adjusted under 35 U.S.C. 154(b) by 169 days.

(21) Appl. No.: 15/708,651

(22) Filed: Sep. 19, 2017

(65) Prior Publication Data
US 2018/0080806 A1    Mar. 22, 2018

(30) Foreign Application Priority Data
Sep. 20, 2016   (DE) .................. 10 2016 011 283

(51) Int. Cl.
*H01R 13/642*    (2006.01)
*G01F 1/69*    (2006.01)
(Continued)

(52) U.S. Cl.
CPC ......... *H01R 13/642* (2013.01); *A61B 5/0878* (2013.01); *A61M 16/0003* (2014.02);
(Continued)

(58) Field of Classification Search
CPC . G01F 1/68; G01F 1/684; G01F 1/688; G01F 1/6888; G01F 1/698; G01F 1/699;
(Continued)

(56) References Cited

U.S. PATENT DOCUMENTS 3,645,133 A * 2/1972 Simeth ................ A61B 5/0878
                                                        73/204.15
4,363,238 A * 12/1982 Willam ............... A61B 5/0878
                                                        600/537
(Continued)

FOREIGN PATENT DOCUMENTS

DE        201 03 966 U1    7/2001

*Primary Examiner* — Justin N Olamit
(74) *Attorney, Agent, or Firm* — McGlew and Tuttle, P.C.

(57) ABSTRACT

A medical device, for example, an anesthesia apparatus or ventilator, including a hot wire sensor (10); a hot wire sensor (10) and a hot wire module (14) for a hot wire sensor (10) are provided. A first hot wire and a second hot wire (26, 28), namely, a measuring wire (26) and a compensation wire (28), are connectable to the hot wire sensor (10), for example, in the form of a hot wire module (14), in an electrically conductive manner. A first contact pair (52, 54) is associated with the measuring wire (26) for contacting same and a second contact pair (56, 58) is associated with the compensation wire (28) for contacting same. The contacts of the second contact pair (56, 58) are configured as leading contacts in relation to at least one of the contacts of the first contact pair (52, 54).

22 Claims, 4 Drawing Sheets

(51) Int. Cl.
*G01F 1/68* (2006.01)
*A61B 5/087* (2006.01)
*A61M 16/00* (2006.01)
*A61M 16/01* (2006.01)
*G01F 15/04* (2006.01)
*G01F 1/699* (2006.01)

(52) U.S. Cl.
CPC ............... *G01F 1/68* (2013.01); *G01F 1/69* (2013.01); *A61M 16/01* (2013.01); *A61M 2016/0033* (2013.01); *A61M 2016/0036* (2013.01); *A61M 2205/3368* (2013.01); *G01F 1/699* (2013.01); *G01F 15/04* (2013.01)

(58) Field of Classification Search
CPC ............ A61B 5/0878; A61M 16/01; A61M 2016/0033; H01R 13/64; H01R 13/642; H01R 2201/20
See application file for complete search history.

(56) References Cited

U.S. PATENT DOCUMENTS

| | | | |
|---|---|---|---|
| 5,230,331 A | | 7/1993 | Rusz et al. |
| 5,676,132 A | | 10/1997 | Tillotson et al. |
| 2001/0039833 A1 | | 11/2001 | Engel et al. |
| 2002/0100474 A1* | | 8/2002 | Kellner ............... A61B 5/0878 |
| | | | 128/200.24 |

* cited by examiner

ANESTHESIA APPARATUS OR VENTILATOR WITH A HOT WIRE SENSOR, HOT WIRE SENSOR AND HOT WIRE SENSOR MODULE FOR A HOT WIRE SENSOR

CROSS REFERENCE TO RELATED APPLICATIONS

This application claims the benefit of priority under 35 U.S.C. § 119 of German Application 10 2016 011 283.2, filed Sep. 20, 2016, the entire contents of which are incorporated herein by reference.

FIELD OF THE INVENTION

The present invention pertains to an anesthesia apparatus or ventilator and to a hot wire sensor of such an anesthesia apparatus or ventilator, which is provided there for acquiring measured values relating to the inhaled and/or exhaled breathing air.

BACKGROUND OF THE INVENTION

The hot wire sensor comprises in a Wheatstone measuring bridge an electrically heated measuring wire and a compensation wire. The measuring bridge releases heat to a medium flowing past, for example, breathing gas, during the measuring operation. The higher the velocity of flow of the medium, the greater is the cooling of the measuring wire. In a manner basically known per se, the flow velocity of the medium in question and hence, for example, a breathing gas volume flow can be determined by means of the measuring bridge on the basis of the resulting temperature fluctuations and the changes in the electrical resistance of the measuring wire, which accompany these temperature fluctuations.

Especially the measuring wire is a part subject to wear of the hot wire sensor and requires replacement at regular intervals. A situation in which a high current flows through the measuring wire and the measuring wire is heated as a result to temperatures exceeding those occurring during the normal operation may occur during the replacement. This reduces the usability (service life) of the measuring wire or leads to a direct destruction of the measuring wire ("burnout") already at the time of the replacement.

Various approaches have been taken to avoid this problem, but these require modifications of the apparatus in question, i.e., for example, of an anesthesia apparatus or ventilator. For example, a protective circuit or the like, whose function is specifically to avoid the overheating or burnout of the measuring wire, is installed within the framework of such a modification. Such modifications are uneconomical.

SUMMARY OF THE INVENTION

Based on this, one object of the present invention is to provide an alternative solution for protecting the measuring wire of a hot wire sensor.

This object is accomplished according to the present invention by means of a hot wire sensor as well as by means of a hot wire module intended and configured for being connected to a circuit of a hot wire sensor, with a hot wire module. The hot wire module comprises a first hot wire comprising a measuring wire, measuring wire contacts for the electrically conductive connection of the measuring wire to the circuit of the hot wire sensor, a second hot wire comprising a compensation wire and compensation wire contacts for the electrically conductive connection of the compensation wire to the circuit of the hot wire sensor. The compensation wire contacts are configured as leading contacts in relation to at least one of the measuring wire contacts for an electrically conductive connection of the compensation wire to the circuit in advance of an electrically conductive connection of the measuring wire to the circuit.

In a hot wire sensor with a hot wire module, which can be electrically and mechanically detachably connected to the circuit thereof, which said module comprises a first hot wire and a second hot wire, namely, a measuring wire and a compensation wire, provisions are made for contacts for the electrically conductive connection of the compensation wire to the circuit of the hot wire sensor to be configured as leading contacts in relation to at least one contact for the electrically conductive connection of the measuring wire to the circuit of the hot wire sensor. Provisions are made in a hot wire module intended and configured for the connection to a circuit of a hot wire sensor, which module comprises a first hot wire and a second hot wire, namely, a measuring wire and a compensation wire, for a second contact pair to be associated with the measuring wire for contacting said measuring wire and for a second contact pair to be associated with the compensation wire for contacting same and for the contacts of the second contact pair to be configured as leading contacts in relation to at least one of the contacts of the first contact pair. As leading contacts, electrical contact is made at the contacts of the compensation wire prior to electrical contact being made at the contacts of the measuring wire when the hot wire module is electrically and mechanically connected to the circuit of the hot wire sensor.

One advantage of the hot wire sensor or hot wire module being provided here is that based on the leading contacts, an undesired premature energization of the measuring wire is avoided with certainty. A special advantage of the innovation being provided here is that a reliable avoidance of an undesired premature energization of the measuring wire is ensured with very simple means, i.e., for example, without mechanically complicated actions and/or without adding to the circuit of the hot wire sensor.

The solution of the invention directed at a hot wire module pertains to the leading contacts being part of the hot wire module. However, this is not absolutely necessary. The leading contacts may also be located on the sides of the hot wire sensor and accordingly belong to the circuit of the hot wire sensor. The aspects of the invention directed at the hot wire sensor are not constrained by specific features regarding the location of the leading contacts. The formulation according to which contacts for the electrically conductive connection of the compensation wire to the circuit of the hot wire sensor are configured as leading contacts relative to at least one contact for the electrically conductive connection of the measuring wire to the circuit of the hot wire sensor comprises and shall comprise the possibility that the leading contacts may be located on the side of the hot wire module or on the side of the rest of the circuit of the hot wire sensor. This shall also always be implied in the following description of the hot wire module and shall also expressly be considered to be covered with this reference by the description presented.

Provisions are made in an embodiment of the hot wire module for the two contacts of the second contact pair to be configured as leading contacts in relation to the two contacts of the first contact pair. This is a peculiarity in relation to the general embodiment of the hot wire module, in which the two contacts of the second contact pair are configured as leading contacts in relation to one of the two contacts of the first contact pair. This embodiment also ensures that the compensation wire is contacted electrically chronologically before the measuring wire during each connection (plugging in) of the hot wire module to the rest of the circuit of the hot wire sensor, so that there can be no flow of current through the measuring wire before the compensation wire is electrically contacted.

Provisions are made in another embodiment of the hot wire module for the contacts of the first contact pair (for contacting the measuring wire) and the contacts of the second contact pair (for contracting the compensation wire) are configured as pins, so that respective pin pairs are obtained, and for the contacts of the second contact pair being configured as leading contacts in relation to at least one of the contacts of the first contact pair or in relation to both contacts of the first contact pair by at least one of the pins of the first contact pair or both pins of the first contact pair being configured such that it is/they are shorter than the pins of the second contact pair. Other contact elements, for example, contact tongues or strip conductors on printed circuit boards, are, of course, also possible instead of pins.

Provisions are made in another embodiment of the hot wire module for this module having means for axially guiding and/or adjusting the hot wire module during the connection to the circuit of the hot wire sensor. Axial direction is defined here as the direction of the plugging operation during the connection of the hot wire module to the circuit of the hot wire sensor. The direction of the plugging operation usually coincides with the orientation of contacts in the form of pins, tongues or the like. A defined position of the hot wire module is guaranteed by means of such adjusting means during the plug-in operation. This ensures that not even an oblique position of the hot wire module can lead to a premature electrical contacting and energization of the measuring wire. Such means may be configured as a groove-and-tongue connection, as it is known, for example, from plug receptacles and the corresponding connector plugs of electrical devices. The contacts of the hot wire module or individual contacts or one of the contacts of the hot wire module may also act as such adjusting means, as this is the case, for example, in case of a so-called Euro plug.

An exemplary embodiment of the present invention will be explained in more detail below on the basis of the drawings. Objects or components corresponding to one another are designated by the same reference numbers in all figures.

The exemplary embodiment shall not be construed as representing a limitation of the present invention. Rather, variants and modifications are possible, especially such variants and combinations at which the person skilled in the art can arrive, for example, by combining or varying individual features described in the general or special part of the specification and contained in the claims and/or in the drawings with respect to the accomplishment of the object and lead to a new subject through features that can be combined.

The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which preferred embodiments of the invention are illustrated.

DESCRIPTION OF THE PREFERRED EMBODIMENTS

Figure 1:
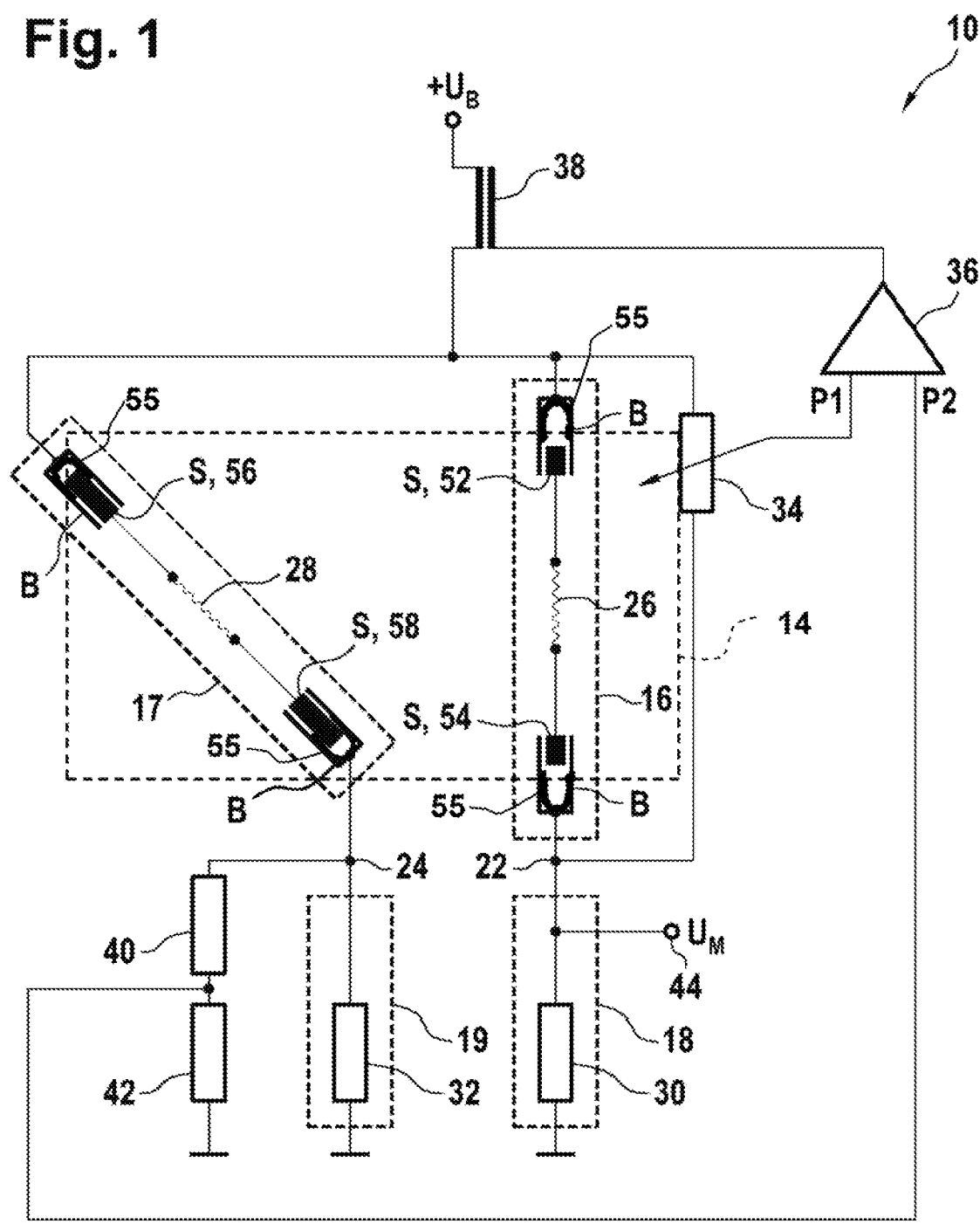
FIG. 1 is a schematic view of a circuit with plugs of a hot wire module according to FIG. 2, which plugs are inserted into jacks, wherein an electrically conductive contacting of the compensation wire chronologically before the contacting of the measuring wire is guaranteed on the basis of the leading contacts comprised by the hot wire module.
Figure 2:
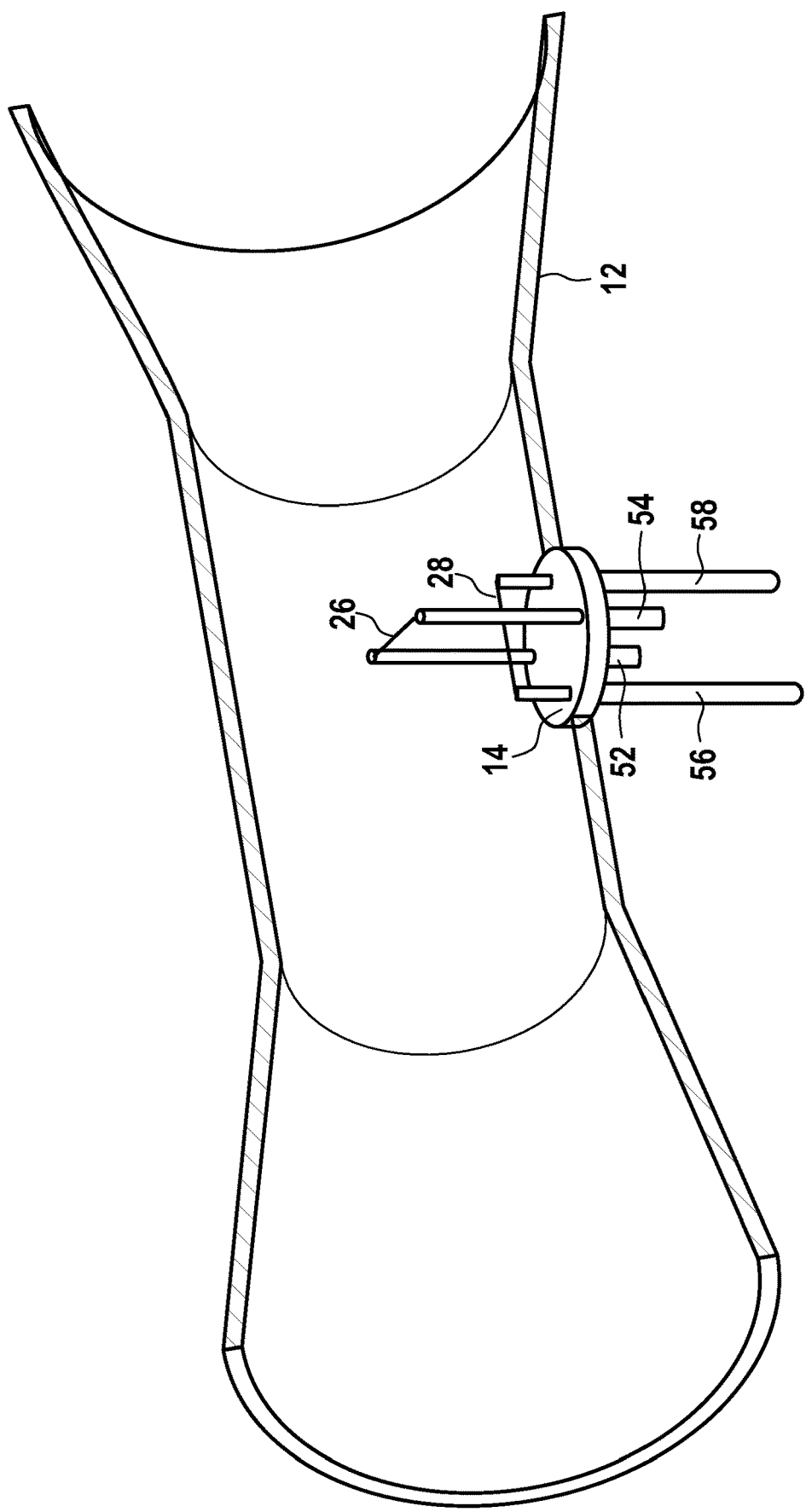
FIG. 2 is a perspective view of a hot wire module, which can be connected to the circuit of the hot wire sensor and which comprises the compensation wire as well as leading contacts for contacting the compensation wire chronologically before the contacting of the measuring wire.

Referring to the drawings, in a schematically simplified form, the view in FIG. 1 shows a circuit of a hot wire sensor 10. The view in FIG. 2 shows, likewise in a schematically simplified form for illustrating an application situation of the hot wire sensor 10, a hot wire module 14 of a hot wire sensor 10, which module is installed in a tube of an anesthesia apparatus or ventilator, not further shown, the tube defining a venturi tube 12. The venturi tube 12 is shown in a sectional view along its central longitudinal axis in the view shown in FIG. 2.

According to FIG. 1, the circuit (hot wire sensor circuitry) of the hot wire sensor 10 comprises a Wheatstone bridge (Wheatstone resistance-measuring bridge), which is called a measuring bridge for short. The measuring bridge is basically known per se, with four bridge branches 16, 17, 18, 19, namely, two bridge branches designated for distinguishing upper bridge branches 16, 17 (first upper bridge branch 16, second upper bridge branch 17) and two bridge branches correspondingly called lower bridge branches 18, 19 (first lower bridge branch 18, second lower bridge branch 19). An upper bridge branch 16, 17 and a lower bridge branch 18, 19 are each connected in series (voltage dividers). The two voltage dividers (bridge branch 16 together with the bridge branch 18, on the one hand, as well as the bridge branch 17 together with the bridge branch 19, on the other hand) are arranged parallel to one another. As is known, there is no potential difference between the center taps 22, 24 of the two voltage dividers.

The hot wire sensor 10 functions, for example, as a measuring instrument for measuring a flow velocity of a quantity of moving gas, for example, of a quantity of gas flowing through the venturi tube 12, and this application is in the foreground here. In case a hot wire sensor 10 is used as a sensor system in conjunction with a control and/or monitoring of the ventilation of a patient by means of an anesthesia apparatus or ventilator, the breathing air being inhaled and/or exhaled is considered to be the quantity of gas being moved and the flow velocity of the breathing air flowing by the hot wire sensor 10 is correspondingly determined by means of the hot wire sensor 10. The inhaled and exhaled air volume can be determined with the flow velocity and the respective known geometry of the air path in which the hot wire sensor 10 is arranged. Whenever reference is made below to gas or a flowing gas volume, air or breathing air shall correspondingly always be implied as a special form of gas that may, in principle, be any gas whatsoever.

For the function of a hot wire sensor (thermoelectric anemometer) 10, the measuring bridge comprises a measuring wire 26, on the one hand, and a compensation wire 28, on the other hand, in the form of very thin wires ("extremely fine" wires, for example, with a diameter of 10 µm to 15 µm) made of a metal with high conductivity, i.e., for example, platinum. The wire module 14 of a hot wire sensor 10 includes both the measuring wire 26 and the compensation wire 28. The wire module 14 of a hot wire sensor 10 is connectable and disconnectable to the hot wire sensor circuitry via a module physical interface.

It can be seen in the view shown in FIG. 2 that in a hot wire sensor 10 inserted into a venturi tube 12, the measuring wire 26 is oriented at right angles or essentially at right angles to the longitudinal axis of the venturi tube 12 and the compensation wire 28 is oriented parallel or essentially parallel to the longitudinal axis of the venturi tube 12. Arrangements of the compensation wire, for example, at an angle in the range of 20° to 60° to the longitudinal axis of the venturi tube 12, are possible in practical embodiments of anemometry with hot wire sensors 10. In the embodiment shown, the measuring wire 26 forms the first upper bridge branch 16 and the compensation wire 28 forms the second upper bridge branch 17. Both wires 26, 28 will hereinafter be called, individually or together, hot wires 26, 28. The first upper bridge branch 16 with the measuring wire 26 forms, together with the lower bridge branch 18 connected to it, a measuring branch of the measuring bridge. The second upper bridge branch 17 with the compensation wire 28 correspondingly forms a compensation branch of the measuring bridge together with the lower bridge branch 19 connected to it.

During the measuring operation, the measuring wire 26 is supplied with a current that is about five times the current flowing through the compensation wire 28. This results from a suitable selection of the resistance values of a measuring resistor 30 in the bridge branch 18 leading to the measuring wire 26, of a reference resistor 32 in the bridge branch 19 leading to the compensation wire 28 as well as of a balancing resistor 34, which is configured, for example, as an adjustable resistor (potentiometer) or in the form of a multiplying D/A converter and which is connected parallel to the measuring wire 26. Temperatures on the order of magnitude of 130° are thus obtained on the measuring wire 26 as well as temperatures on the order of magnitude of 30° are thus obtained on the compensation wire 28 during the operation of the hot wire sensor 10 and at an ambient temperature of about 20°. The balanced state (state of equilibrium) of the measuring bridge is established by suitably setting the balancing resistor 34.

When thermal energy is removed from the measuring wire 26 by gas flowing past, for example, breathing air, during the measuring operation, a current state of equilibrium of the measuring bridge is upset. The electrical resistance of the measuring wire 26 will thus also drop with decreasing temperature. This is compensated by the circuit to reestablish the equilibrium by means of an increased current feed into the measuring wire 26.

The current feed/additional current supply takes place by means of a combination of an operational amplifier circuit 36 as well as of a circuit component 38 that can be energized therewith such that a difference in resistance, resulting from a temperature difference, between the two hot wires 26, 28 (measuring wire 26, compensation wire 28) and a potential difference associated therewith between the center taps 22, 24 of the two voltage dividers is maintained at a constant value. The operational amplifier circuit 36 is optionally configured in the form of precisely one operational amplifier. An electrically energizable switch, especially an electronically energizable switch in the form of a bipolar or field-effect transistor of the like, may be considered for use as a circuit component 38. The operational amplifier circuit 36 is indirectly connected to the two center taps 22, 24 and thus the operational amplifier circuit 36 compares the potentials P1 and P2 present there. In the embodiment shown, the operational amplifier circuit 36 is connected to the center tap 22 on the measuring wire 26 via the balancing resistor 34 connected parallel to the measuring wire 26, on the one hand, and to the center tap 24 on the compensation wire 28 via a resistor network 40, 42, on the other hand. In case of a potential difference detected by means of the operational amplifier circuit 36, the circuit component 38 is energized via the output of the operational amplifier circuit 36 and the connection to the operating voltage $U_B$ is thus established, so that current flows into the measuring bridge, is divided between the "right" bridge branches 16, 18 and the "left" bridge branches 17, 19 corresponding to the resistance values, and thus leads to an increase in the temperature of the previously cooled measuring wire 26. The current now flowing over the measuring wire 26 is an indicator of the total quantity of gas that has flowed past the measuring wire 26. For example, the voltage dropping over the measuring resistor 30 based on the current is considered for the measurement. The measuring resistor 30 acts as a serial measuring shunt in the embodiment being shown and the measuring resistor 30 is preferably a precision resistor, for example, a precision resistor with a resistance tolerance in the range of 0.1% to 0.5%. The voltage dropping over the measuring resistor 30 can be tapped at a measuring voltage terminal 44 as a measured voltage $U_M$. The compensation wire 28 is used, so to speak, as a resistance-measuring sensor to compensate changes in the gas temperature during the ongoing operation of the hot wire sensor 10.

Without the features of the module 14 according to the invention and without a protective circuit against excessive energization of the hot wires 26, 28, a situation could arise in which the current flows through the measuring wire 26 chronologically before the flow through the compensation wire 28. In such a situation the current would not flow through the measuring wire 26 on the basis of the ratios (for example, 5:1, see above) set by the configuration of the bridge circuit. A maximum current would rather flow for a certain time period through the measuring wire 26, as would otherwise happen, for example, in case of maximum cooling of the measuring wire 26, i.e., in case of maximum flow rate (>150 L/minute) during the measuring operation. This maximum current flows as long as current also flows through the compensation wire 28, and the current flow is divided in the bridge circuit between the two hot wires 26, 28 and is otherwise obtained from the potential difference present at the input of the operational amplifier circuit 36. The consequence of such energization of the measuring wire 26 chronologically before that of the compensation wire 28 is that the measuring wire 26 is operated markedly above an actually intended operating temperature of <180° C. during this time. The measuring wire 26 would in such case reach temperatures of up to 300° C. and higher. This unintentionally elevated heating may affect the shape of the measuring wire 26 and the state of the material thereof. This leads to possible consequential problems, for example, aging of the conductor material used, for example, platinum, and/or changes in the resistance/temperature characteristic of the conductor material used. This may in turn lead to reduced service life of the measuring wire 26 and hence of the hot wire sensor 10 as a whole. Regardless of this, changes in the resistance/temperature characteristic may cause a flow characteristic, which is used as the basis for the analysis of the measured voltage $U_M$ and is stored in the particular apparatus, which uses the hot wire sensor 10 as a sensor system, not to be able to be used with the required accuracy any longer, so that flow velocities and/or gas volumes determined on the basis of the measured voltage $U_M$ contain errors.

Aging of the measuring wire 26 or of the measuring wire 26 and of the compensation wire 28 also occurs during the normal measuring operation, so that the hot wires 26, 28, being parts subject to wear, need to be replaced at regular intervals, while the rest of the circuit shown in FIG. 1, can be used over a long time period. To facilitate the replacement of the hot wires 26, 28, these are integrated in the form of a module 14 (hot wire module 14; FIGS. 1 and 2) that can be connected to the circuit according to FIG. 1 in an electrically conductive manner. The hot wire module 14 comprises, in the form of individual pin-shaped plug contacts (plugs), a first contact pair 52, 54 and a second contact pair 56, 58, so that a four-pole connector and a four-pole module are obtained as a whole. The second contact pair 56, 58 is likewise associated with the compensation wire 28 comprised by the hot wire module 14.

The view in FIG. 1 shows plugs S that are a part of the module 14 and the jacks B, with each plug S belonging to one of the two contact pairs 52, 54; 56, 58 of the hot wire module 14 and with each jack B, having electrical contact surfaces 55, allowing the insertion of a plug S, i.e., of a contact 52-58 each of the two contact pairs 52, 54; 56, 58. The geometric arrangement of the jacks B of the hot wire sensor 10 and of the plugs S of the hot wire module 14 is selected in this case to be such that the hot wire module 14 can be connected to the rest of the circuit of the hot wire sensor 10 in an electrically conductive manner only as intended, i.e., only in exactly one orientation/plug-in position. It should be noted for the sake of completeness that the reference of plugs S on the side of the hot wire module 14 and of jacks B on the side of the rest of the circuit of the hot wire sensor 10 pertains only to the embodiment being shown and shall not be interpreted as representing a limitation in any way. Likewise, the hot wire module 14 may have jacks B for receiving plug-type contacts and the rest of the circuit of the hot wire sensor 10 may have corresponding plugs S for insertion into the jacks B of the hot wire module 14. Mixed configurations are likewise conceivable, such that the hot wire module 14 has both plugs S as well as jacks B and the rest of the circuit of the hot wire sensor 10 has corresponding jacks B and plugs S. To avoid the above-mentioned unfavorable premature energization of the measuring wire 26, leading contacts 56, 58 are provided for contacting the compensation wire 28, especially leading contacts are used on the side of the hot wire module 14 or on the side of the rest of the circuit of the hot wire sensor 10. This is a chronological contact means of the module 14, for chronologically electrically connecting the contacts of the compensation wire 28 prior to connecting the contacts of the measuring wire 26. During the action of connecting the module 14, the pins/contacts 56, 58 of the compensation wire 28 are electrically connected earlier in time to the associated electrical contact surfaces 55, and to the other parts of the Wheatstone Bridge 16, 17, 18, 19, and the resistor network 30, 32, 34, 40, 42 and the electronics 36, 38 than the pins/contacts 52, 54 of the measuring wire 26. This occurs, because the pins of the measuring wire 26 are shorter than the pins of the compensation wire 28.

In the view shown in FIG. 2, the leading contacts 56, 58 are shown in the form of longer contact pins (plugs S) compared to the contacts 52, 54 of the measuring wire 26 as a part of a chronological contact means for chronologically electrically connecting the contacts of the compensation wire 28 prior to connecting the contacts of the measuring wire 26. The chronological contact means is part of the module 14. Based on the greater length compared to the contact 52, 54, the leading contacts 56, 58 of the compensation wire 28 come into electrically conductive contact with the respective jacks B provided for receiving the plugs S before the contacts 52, 54 of the measuring wire 26 at the time of connecting the hot wire module 14 to the rest of the circuit of the hot wire sensor 10. Leading contacts are, in principle, known per, for example, a so-called USB plug comprises leading contacts. Leading contacts 56, 58 for contacting the compensation wire 28 guarantee that the electrically conductive connection of the compensation wire 28 to the rest of the circuit of the hot wire sensor 10 takes place chronologically before the electrically conductive connection of the measuring wire 26 to the circuit of the hot wire 10. The energization of the measuring wire 26 chronologically after the energization of the compensation wire 28, which is ensured hereby, guarantees that the otherwise possible overheating of the measuring wire 26 is avoided with certainty. It is achieved that the process of contacting the hot wire module 14 with the rest of the circuit of the hot wire sensor 10, and hence the electrically conductive contacting of the measuring wire 26 and of the compensation wire 28, are reproducible in such a manner that the establishment of the connection always leads to reproducibly defined operating states contributing to the improvement of the service life of the hot wires 26, 28.

The leading contacts 56, 58 for contacting the compensation wire 28 are configured in the embodiment shown in such a form that the length (depth of insertion) of all jacks B is equal and the effective length of the plugs S intended for contacting the compensation wire 28 (second contact pair 56, 58) is greater than the effective length of the plugs S intended for contacting the measuring wire 26 (first contact pair 52, 54). The effective length of a plug S is defined here as the length of the plug S that can be inserted into the respective jack B during the contacting of a jack B.

In FIG. 1, to illustrate the action of the leading contacts of the hot wire module 14, the plugs S of this module (first contact pair 52, 54; second contact pair 56, 58) are shown with schematically simplified, different lengths. The lengths of the plugs S that form the second contact pair 56, 58 for the electrically conductive contacting of the compensation wire 28 are configured such that they are longer and are correspondingly also shown as being longer than the plugs S that form the first contact pair 52, 54 for the electrically conductive contacting of the measuring wire 26. The view shall illustrate that when connecting a hot wire module 14 to the rest of the circuit of the hot wire sensor 10, the plugs S of the contact pair 56, 58 are already in an electrically conductive contact with the respective jacks B before the plugs S of the first contact pair 52, 54 come into electrically conductive contact with jacks B intended for receiving them.

Figure 3:
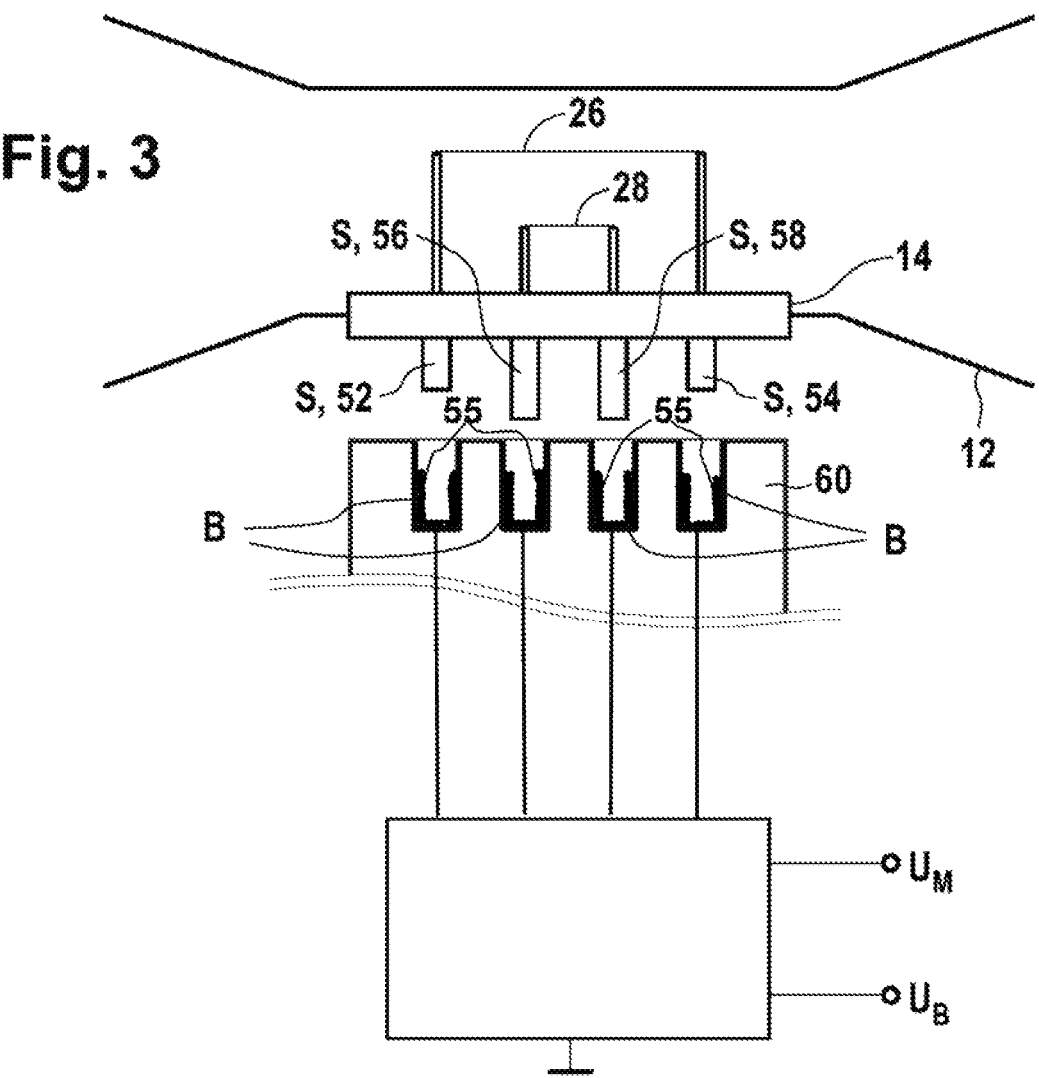
FIG. 3 is a schematic lateral view of the jacks of the circuit of the hot wire sensor according to FIG. 1 and FIG. 2, showing a hot wire module according to FIG. 2 with plugs thereof, for being inserted into the jacks, wherein individual plugs are configured as leading contacts, so that an electrically conductive contacting of the compensation wire is achieved chronologically before the contacting of the measuring wire.

The view in FIG. 3 shows the same features in a schematically simplified lateral view, the situation of the arrangement of the measuring wire 26 and compensation wire 28 essentially at right angles corresponding here to the arrangement shown in FIG. 2. For reasons of clarity, this is not shown in the simplified lateral view shown in this FIG. 4, as it is possible, for example, in the form of a perspective view. The jacks B of the circuit of the hot wire sensor 10 are shown in the lower area of the view and the plugs S of the hot wire module 14, namely, the two "shorter" plugs S forming the first contact pair 52, 54 and the plugs S of the second contact pair 56, 58, which are "longer" compared thereto, are shown in the upper area. The jacks B are combined in a connection or jack component 60, and electrically conductive connections lead via a connection cable originating from the connection component 60 to the rest of the circuit of the hot wire sensor 10 (see FIG. 1 and FIG. 3).

It can also be seen in the schematically simplified view shown in FIG. 3 that during a movement of the hot wire module 14 in the direction of the longitudinal extension of the plugs S or during a corresponding movement of the connection component 60, i.e., during the connection of the hot wire module 14 to the connection component 60, the plugs S of the contact pair 56, 58, which plugs act as leading contacts 56, 58, come into contact with the jacks B provided for receiving them sooner than do the plugs S of the first contact pair 52, 54 and the jacks B intended for receiving them.

In the embodiments shown in the figures, the plugs S (pins) of the contacts 52, 54; 56, 58, forming the chronological contact means for chronologically electrically connecting the contacts of the compensation wire 28 prior to connecting the contacts of the measuring wire 26, have equal lengths in pairs (plug-pin pair 52, 54; plug-pin pair 56, 58). This is not a necessary requirement. For example, one of the plugs of a plug pair 52, 54; 56, 58 may be longer or longer and thicker than all other plugs 52-58 and it may act as a means for the axial adjustment/guiding of the hot wire module 14 during the connection to the circuit of the hot wire sensor 10.

Figure 4:
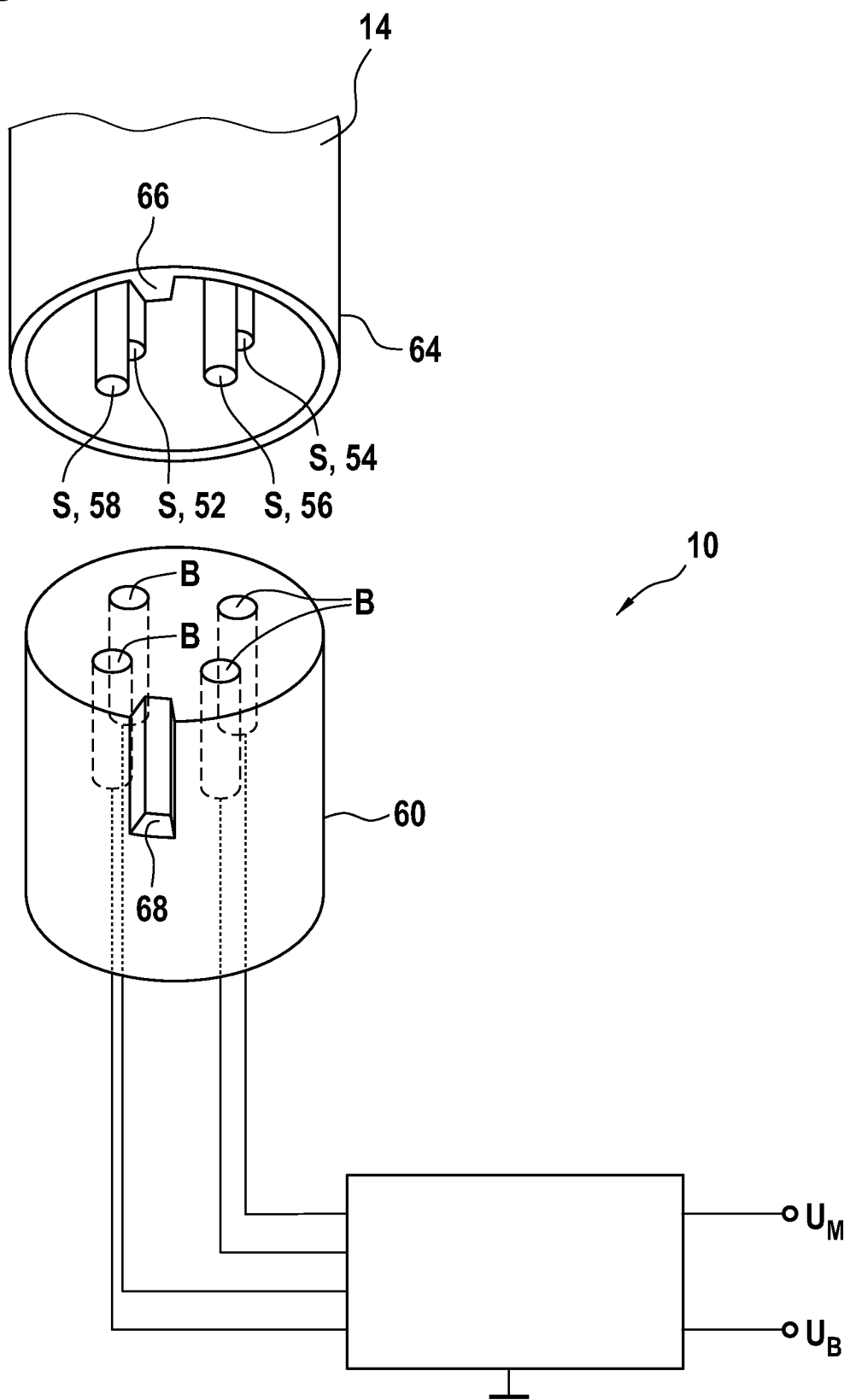
FIG. 4 is a perspective view showing an embodiment of the hot wire module and of a connection component provided for connecting same with means for the axial adjustment of the hot wire module.

An alternative or additional embodiment of adjustment means for the axial adjustment/guiding of the hot wire module 14 during the connection to the circuit of the hot wire sensor 10 is shown in the view in FIG. 4. It is shown there that the hot wire module 14 has a hollow cylindrical collar 64 enclosing the contacts 52-58, and at least one projection 66 oriented in the direction of the longitudinal axis of the hollow cylindrical collar 64 rises up on an inner jacket surface of the collar 64. Fitting thereto, the connection component 62 has a cylindrical configuration in at least some sections and has in its jacket surface at least one recess 68, which is oriented in the direction of the longitudinal axis of the cylindrical section of the connection component 62 and parallel to the contacts 52-58. The projection 66 or each projection 66 in the interior of the collar 64 of the hot wire module 14 and the recess 68 or each recess 68 in the jacket surface of the connection component 60 are configured correspondingly, such that the recess 68 or each recess 68 receives a projection 66 each in a positive-locking manner. The projection 66 and the recess 68 or one projection 66 and one recess 68 receiving the projection each likewise act as means for axially adjusting/guiding the hot wire module 14 during the connection to the rest of the circuit of the hot wire sensor 10. It is guaranteed by means of the axial adjustment that the hot wire module 14 cannot be "tilted" during the connection to the rest of the circuit of the hot wire sensor 10 and the function of the leading contacts 56, 58 for the protection of the measuring wire 26 is not circumvented with such tilting. As is shown, the adjustment means for the axial adjustment, i.e., for example, the projection 66 or each projection 66 and the recess 68 or each respective recess 68 come into contact with one another chronologically before the plugs S and the jacks B do in a special embodiment, so that the axial adjustment is always guaranteed before an electrically conductive contact is established. This is achieved in the embodiment shown by the depth of the space defined by the collar 64 with the contacts 52-58 (plugs S) located in it and oriented parallel to one another being greater than the greatest length of the contacts 52-58, the projection 66 or each projection extending on the inner surface of the collar 64 at least farther "downward" than do the contacts 52-58, i.e., for example, up to the edge of the collar 64. The projection 66 or each projection 66 and the recess 68 or each recess 68 intended for receiving same in a positive-locking manner assume a dual function. On the one hand, the function as a means for the axial adjustment of the hot wire module 14 arises. On the other hand, an additional or alternative possibility arises for a coding, which guarantees that the hot wire module 14 can be connected to the rest of the circuit of the hot wire sensor 10 in an electrically conductive manner only as intended, i.e., only in precisely one orientation/plug-in position.

The essence of the innovation being proposed here can finally be briefly summarized as follows: Given are a medical device, for example, an anesthesia apparatus or ventilator, with a hot wire sensor 10; a hot wire sensor 10 and a hot wire module 14 for a hot wire sensor 10. A first hot wire and a second hot wire, 26, 28, namely, a measuring wire 26 and a compensation wire 28, can be connected to the hot wire sensor 10 in an electrically conductive manner, for example, in the form of a hot wire module 14 comprising the measuring wire 26 and the compensation wire 28. A first contact pair 52, 54 is associated with the measuring wire 26 for contacting same. The contacts of the second contact pair 56, 58 for the electrical contacting of the compensation wire 28 are configured as leading contacts in relation to at least one of the contacts of the first contact pair 52, 54 for the electrical contacting of the measuring wire 26. It is guaranteed that the measuring wire 26 will not be damaged or destroyed during the connection due to the fact that it is ensured by means of the leading contacts that the measuring wire 26 is never energized before the compensation wire 28 and it is rather ensured in any case when connecting the hot wires 26, 28 to the rest of the circuit of the hot wire sensor 10 that the compensation wire 28 is energized before the measuring wire 26.

While specific embodiments of the invention have been shown and described in detail to illustrate the application of the principles of the invention, it will be understood that the invention may be embodied otherwise without departing from such principles.

What is claimed is:

1. A hot wire sensor comprising:
   a hot wire sensor circuit comprising a measuring contact pair and a compensation contact pair, the measuring contact pair being disposed in a predetermined position relative to the compensation contact pair; and
   a hot wire module for electrically and mechanically detachably connecting to the hot wire sensor circuit, via the measuring contact pair and the compensation contact pair, wherein the hot wire module comprises:
   a first hot wire comprising a measuring wire;

a second hot wire comprising a compensation wire; and
a chronological contact means for chronologically electrically connecting the compensation wire to the hot wire sensor circuit prior to electrically connecting the measuring wire to hot wire sensor circuit, the chronological contact means comprising a contact pair arrangement comprising measuring wire contacts for an electrically conductive contact connection of the measuring wire to the hot wire sensor circuit in a state of a mechanical connection of the hot wire module to the hot wire sensor circuit and compensation wire contacts for an electrically conductive contact connection of the compensation wire to the hot wire sensor circuit in the state of the mechanical connection of the hot wire module to the hot wire sensor circuit, the chronological contact means chronologically electrically contact connecting the compensation wire contacts to the compensation contact pair prior to electrically contact connecting the measuring wire contacts to the measuring contact pair, as the hot wire module is being mechanically connected to the hot wire sensor circuit to change from a mechanically unconnected state to the state of the mechanical connection.

2. A hot wire sensor according to claim 1, wherein the chronological contact means is formed with the compensation wire contacts configured as leading contacts in relation to at least one of the measuring wire contacts for an electrically conductive connection of the compensation wire to the hot wire sensor circuit in advance of an electrically conductive connection of the measuring wire to the hot wire sensor circuit.

3. A hot wire module for an electrically and mechanically detachable connection to a measuring contact pair and a compensation contact pair of a circuit of a hot wire sensor, the hot wire module comprising:
a first hot wire comprising a measuring wire;
a second hot wire comprising a compensation wire; and
a chronological contact means for chronologically electrically connecting the compensation wire to the circuit of the hot wire sensor prior to connecting the measuring wire to the circuit of the hot wire sensor, the chronological contact means comprising a contact pair arrangement comprising measuring wire contacts for an electrically conductive contact connection of the measuring wire to the circuit of the hot wire sensor, upon completing a mechanical connection of the hot wire module to the circuit of the hot wire sensor, and compensation wire contacts for an electrically conductive contact connection of the compensation wire to the circuit of the hot wire sensor, upon completing the mechanical connection of the hot wire module to the circuit of the hot wire sensor, the chronological contact means chronologically electrically contact connecting the compensation wire contacts to the compensation contact pair prior to electrically contact connecting the measuring wire contacts to the measuring contact pair, as the hot wire module is mechanically connected to the circuit of the hot wire sensor.

4. A hot wire module according to claim 3, wherein the chronological contact means is formed with a configuration of the contact pair arrangement wherein the contacts of the compensation wire contact pair are configured as leading contacts in relation to at least one of the contacts of the measuring wire contact pair for an electrically conductive connection of the compensation wire to the circuit in advance of an electrically conductive connection of the measuring wire to the circuit.

5. A hot wire module in accordance with claim 4, wherein the contacts of the compensation wire contact pair are configured as leading contacts in relation to both contacts of the measuring wire contact pair.

6. A hot wire module in accordance with claim 4, wherein the contacts of the compensation wire contact pair and the contacts of the measuring wire contact pair are configured as pins, and wherein the contacts of the compensation wire contact pair are configured as leading contacts in relation to at least one of the contacts of the measuring wire contact pair, by at least one of the pins of the measuring wire contact pair being configured as being shorter than the pins of the compensation wire contact pair.

7. A hot wire module in accordance with claim 5, wherein the contacts of the compensation wire contact pair and the contacts of the measuring wire contact pair are configured as pins, and wherein the contacts of the compensation wire contact pair are configured as leading contacts in relation to at least one of the contacts of the measuring wire contact pair, by at least one of the pins of the measuring wire contact pair being configured as being shorter than the pins of the measuring wire contact pair.

8. A hot wire module in accordance with claim 3, further comprising adjustment means for axially adjusting the hot wire module during connection to the circuit of the hot wire sensor.

9. A hot wire sensor comprising:
hot wire sensor circuitry with a module physical interface comprising a measuring contact pair and a compensation contact pair, the measuring contact pair being disposed in a predetermined position relative to the compensation contact pair; and
a hot wire module configured to be electrically and mechanically connectable and disconnectable from the hot wire sensor circuitry via the module physical interface, the hot wire module comprising:
a first hot wire comprising a measuring wire;
a second hot wire comprising a compensation wire; and
a chronological contact means for chronologically electrically connecting the compensation wire to the hot wire sensor circuitry prior to electrically connecting the measuring wire to the hot wire sensor circuitry, the chronological contact means comprising a contact pair arrangement comprising measuring wire contacts for an electrically conductive contact connection of the measuring wire to the measuring contact pair of the module physical interface, upon completing a mechanical connection of the hot wire module to the module physical interface, and compensation wire contacts for an electrically conductive contact connection of the compensation wire to the compensation contact pair of the module physical interface, upon completing the mechanical connection of the hot wire module to the module physical interface, the chronological contact means chronologically electrically contact connecting the compensation wire contacts to the compensation contact pair prior to electrically contact connecting the measuring wire contacts to the measuring contact pair, as the hot wire module is mechanically connected to the module physical interface.

10. A hot wire sensor according to claim 9, wherein the chronological contact means is formed with a configuration of the contact pair arrangement of the hot wire module wherein the contacts of the compensation wire contact pair are configured as leading contacts in relation to at least one of the contacts of the measuring wire contact pair for an electrically conductive connection of the compensation wire to the circuit in advance of an electrically conductive connection of the measuring wire to the circuit.

11. A hot wire sensor in accordance with claim 10, wherein the contacts of the compensation wire contact pair are configured as leading contacts in relation to both contacts of the measuring wire contact pair.

12. A hot wire sensor in accordance with claim 10, wherein the contacts of the compensation wire contact pair and the contacts of the measuring wire contact pair are configured as pins, and wherein the contacts of the compensation wire contact pair are configured as leading contacts in relation to at least one of the contacts of the measuring wire contact pair, by at least one of the pins of the measuring wire contact pair being configured as being shorter than the pins of the compensation wire contact pair.

13. A hot wire sensor in accordance with claim 11, wherein the contacts of the compensation wire contact pair and the contacts of the measuring wire contact pair are configured as pins, and wherein the contacts of the compensation wire contact pair are configured as leading contacts in relation to at least one of the contacts of the measuring wire contact pair, by at least one of the pins of the measuring wire contact pair being configured as being shorter than the pins of the compensation wire contact pair.

14. A hot wire sensor in accordance with claim 10, wherein the hot wire module further comprises adjustment means for axially adjusting and guiding a position of the hot wire module as the hot wire module is physically connected to the module physical interface of the circuit of the hot wire sensor.

15. A medical device comprising a hot wire sensor comprising:
   hot wire sensor circuitry with a module physical interface; and
   a hot wire module configured to be electrically and mechanically connectable and disconnectable from the hot wire sensor circuitry via the module physical interface, the hot wire module comprising:
   a first hot wire comprising a measuring wire;
   a second hot wire comprising a compensation wire; and
   a chronological contact means for chronologically electrically connecting the compensation wire to the hot wire sensor circuitry prior to electrically connecting the contacts of the measuring wire to the hot wire sensor circuitry, the chronological contact means comprising a contact pair arrangement comprising measuring wire contacts for an electrically conductive contact connection of the measuring wire to the measuring contact pair of the module physical interface, upon completing a mechanical connection of the hot wire module to the module physical interface, and compensation wire contacts for an electrically conductive contact connection of the compensation wire to the compensation contact pair of the module physical interface, upon completing the mechanical connection of the hot wire module to the module physical interface, the chronological contact means chronologically electrically contact connecting the contacts of the compensation wire to the compensation contact pair prior to electrically contact connecting the contacts of the measuring wire to the measuring contact pair, as the hot wire module is mechanically connected to the module physical interface.

16. A medical device in accordance with claim 15, wherein the module is configured with the contacts of the compensation wire contact pair configured as leading contacts in relation to at least one of the contacts of the measuring wire contact pair for an electrically conductive connection of the compensation wire to the circuit in advance of an electrically conductive connection of the measuring wire to the circuit.

17. A medical device in accordance with claim 16, wherein the contacts of the compensation wire contact pair are configured as leading contacts in relation to both contacts of the measuring wire contact pair.

18. A medical device in accordance with claim 16, wherein the contacts of the compensation wire contact pair and the contacts of the measuring wire contact pair are configured as pins, and wherein the contacts of the compensation wire contact pair are configured as leading contacts in relation to at least one of the contacts of the measuring wire contact pair, by at least one of the pins of the measuring wire contact pair being configured as being shorter than the pins of the compensation wire contact pair.

19. A medical device in accordance with claim 17, wherein the contacts of the compensation wire contact pair and the contacts of the measuring wire contact pair are configured as pins, and wherein the contacts of the compensation wire contact pair are configured as leading contacts in relation to at least one of the contacts of the measuring wire contact pair, by at least one of the pins of the measuring Lamps wire contact pair being configured as being shorter than the pins of the compensation wire contact pair.

20. A medical device in accordance with claim 16, wherein the hot wire module further comprises adjustment means for axially adjusting the hot wire module as the hot wire module is physically connected to the module physical interface of the circuit of the hot wire sensor.

21. A medical device in accordance with claim 16, wherein the medical device is an anesthesia apparatus.

22. A medical device in accordance with claim 16, wherein the medical device is a ventilator.

* * * * *